(12) United States Patent
Dadd et al.

(10) Patent No.: US 11,633,590 B2
(45) Date of Patent: *Apr. 25, 2023

(54) HEARING PROSTHESIS ELECTRODE ARRAY WITH RESILIENTLY FLEXIBLE TIP MEMBER

(71) Applicant: Cochlear Limited, Macquarie University (AU)

(72) Inventors: Fysh Dadd, Lane Cove (AU); Claudiu Treaba, Richmond (AU); Peter Gibson, South Coogee (AU)

(73) Assignee: Cochlear Limited, Macquarie University (AU)

( * ) Notice: Subject to any disclaimer, the term of this patent is extended or adjusted under 35 U.S.C. 154(b) by 1325 days.

This patent is subject to a terminal disclaimer.

(21) Appl. No.: 15/248,001

(22) Filed: Aug. 26, 2016

(65) Prior Publication Data

US 2017/0080212 A1 Mar. 23, 2017

Related U.S. Application Data

(63) Continuation of application No. 12/683,424, filed on Jan. 6, 2010, now Pat. No. 9,427,568, which is a continuation of application No. 10/825,358, filed on Apr. 16, 2004, now abandoned.

(30) Foreign Application Priority Data

Apr. 17, 2003 (AU) ................ 2003901868

(51) Int. Cl.
*A61N 1/05* (2006.01)

(52) U.S. Cl.
CPC ................ *A61N 1/0541* (2013.01)

(58) Field of Classification Search
CPC .......... A61N 1/05; A61N 1/0541; A61N 1/36; A61N 1/36036
USPC ........................................ 607/137
See application file for complete search history.

(56) References Cited

U.S. PATENT DOCUMENTS

| | | | |
|---|---|---|---|
| 1,146,292 A | 7/1915 | Wappler | |
| 5,123,422 A | 6/1992 | Charvin | |
| 5,545,219 A * | 8/1996 | Kuzma | ............... A61N 1/05 607/137 |
| 6,078,841 A * | 6/2000 | Kuzma | ............... A61N 1/0541 607/137 |
| 6,119,044 A | 9/2000 | Kuzma | |
| 6,125,302 A | 9/2000 | Kuzma | |
| 6,149,657 A * | 11/2000 | Kuzma | ............... A61N 1/0541 606/129 |

(Continued)

OTHER PUBLICATIONS

Applied Silicone Corporation, Product Information Sheet, Implant Grade Liquid Silicone Rubber, 3 pages, Aug. 20, 2002.

*Primary Examiner* — Christopher A Flory
(74) *Attorney, Agent, or Firm* — Pilloff Passino & Cosenza LLP; Martin J. Cosenza (57) ABSTRACT

A tip member for inserting into the cochlea, a device comprising: an elongate member including at least one electrode mounted thereon; and a tip member extending distally from a distal end of the elongate member, the tip member comprising a tapered portion tapering distally and a blunt end portion at a distal end of the tapered portion, wherein the tip member is resiliently flexible, and a method for making such a device.

22 Claims, 5 Drawing Sheets

(56) References Cited

U.S. PATENT DOCUMENTS

| | | | | |
|---|---|---|---|---|
| 6,163,729 A | * | 12/2000 | Kuzma | A61N 1/0541 607/137 |
| 6,195,586 B1 | | 2/2001 | Kuzma | |
| 6,374,143 B1 | * | 4/2002 | Berrang | A61N 1/0541 600/379 |
| 6,421,569 B1 | * | 7/2002 | Treaba | A61N 1/0541 607/137 |
| 7,315,763 B2 | * | 1/2008 | Kuzma | A61N 1/0541 607/137 |
| 2002/0029074 A1 | * | 3/2002 | Treaba | A61N 1/0541 607/137 |
| 2003/0125785 A1 | * | 7/2003 | Kuzma | A61N 1/0541 607/116 |
| 2003/0181967 A1 | * | 9/2003 | Dadd | A61N 1/0541 607/122 |
| 2004/0122501 A1 | * | 6/2004 | Dadd | A61N 1/0541 607/137 |
| 2004/0127968 A1 | * | 7/2004 | Kuzma | A61N 1/0541 607/137 |
| 2004/0220651 A1 | * | 11/2004 | Kuzma | A61N 1/0541 607/137 |
| 2006/0235500 A1 | * | 10/2006 | Gibson | A61N 1/0541 607/137 |
| 2008/0027527 A1 | * | 1/2008 | Kuzma | A61N 1/0541 607/137 |
| 2011/0276118 A1 | * | 11/2011 | Kuzma | A61N 1/0541 607/137 |

* cited by examiner

HEARING PROSTHESIS ELECTRODE ARRAY WITH RESILIENTLY FLEXIBLE TIP MEMBER

CROSS-REFERENCE TO RELATED APPLICATIONS

This application is a continuation of U.S. patent application Ser. No. 12/683,424, filed Jan. 6, 2010, which is a continuation of U.S. patent application Ser. No. 10/825,358, filed Apr. 16, 2004, which claims priority from Australian Provisional Patent Application No. 2003901868, entitled "Electrode Array with Bendable Tip" filed Apr. 17, 2003, each of which are hereby incorporated by reference herein. To the extent appropriate, a claim of priority is made to each of the above disclosed applications.

BACKGROUND

Field of the Invention

The present invention relates generally to hearing prostheses, and more particularly, to a hearing prosthesis electrode array with a resiliently flexible tip member.

Related Art

Electrode arrays, such as cochlear implant electrode arrays, generally consist of a plurality of electrode elements which are adapted to apply electrical stimulation to surrounding tissue to stimulate the surrounding nerves. In cochlear implant applications, the electrode array is implanted within the cochlea of a recipient and applies stimulation to the auditory nerves via a series of electrode elements, in accordance with a set stimulation pattern, controlled by an implanted stimulator unit.

The implanted stimulator unit typically applies the stimulation in a manner which is representative of a detected acoustic signal, such that the stimulation pattern applied by the electrode array stimulates the auditory nerves and elicits a sensation that closely resembles the natural sensation of the detected acoustic signal.

In this regard, it is important that when implanting electrode arrays in sensitive regions of the body, such as the cochlea, that the electrode array be flexible enough to reduce damage to the sensitive structures of the surrounding tissue, and yet be rigid enough to ensure that the general shape and form of the electrode array is maintained during the insertion procedure such that the electrode array can perform as intended.

In electrode arrays of the type used for implantation in the cochlea, it has been found that the tip of the array plays an important role during the insertion procedure. In this regard, there have been attempts to design the tip of the electrode array in a manner that reduces the possibility of the tip of the electrode array from puncturing or abrading the sensitive tissues of the cochlea and causing damage to the nerve structures which the implant is attempting to stimulate.

One such early attempt is described in Australian Patent No. 582264 to Clark et al. This patent discloses the provision of tip or distal end of the electrode array being provided with at least one discontinuity that increases the flexibility of the tip. The tip is generally an extension of the existing electrode array and is made from the same material, but is extending beyond the most distal electrode element.

One problem with such a design is that the tips were typically relatively too flexible such that during the insertion process the tip would catch on the wall of the cochlea and cause the array to bend back on itself, thereby potentially causing more damage to the cochlea than would ordinarily be the case should the flexible tip not be provided. Such a situation can also result in an implant being incorrectly positioned from the auditory nerve potentially reducing the effectiveness of the array in capturing and stimulating the appropriate nerves. Further, such a situation where the array folds upon itself can cause unwanted interaction or shorting between electrode elements that may be touching, thereby reducing the number of electrodes that may be operational for stimulation.

Other designs have also considered providing an extended flexible tip of a lead or electrode array to aid in insertion, such as that described in EP 0 919 254 to Bakels et al. However, as mentioned above, such tips have all been designed with flexibility in mind rather than stability of the tip, hence all suffer from similar problems as identified above.

SUMMARY

In one aspect of the present invention, a hearing prosthesis is disclosed. The hearing prosthesis comprises an elongate member, configured to be implanted into a duct of a recipient's cochlea, having a preformed curved orientation, proximal and distal ends, electrodes disposed thereon, and a longitudinally-extending lumen for receiving a stiffening element; and a tip member, extending distally from the distal end of the elongate member, configured to have a substantially uniform bending stress distribution in an axial direction, and a length sufficiently short to avoid substantially damaging walls of the duct when the elongate member is in a fully implanted location in the cochlea, and sufficiently long to guide the elongate member through the duct to the fully implanted location as the elongate member adopts its preformed curved orientation in response to withdrawal of the stiffening element from the lumen.

In another aspect of the present invention, a hearing prosthesis is disclosed. The hearing prosthesis comprises an elongate member, configured to be implanted into a duct of a recipient's cochlea, having a preformed curved orientation, proximal and distal ends, electrodes disposed thereon, and a longitudinally-extending lumen for receiving a stiffening element; and a tip member, extending distally from the distal end of the elongate member, having a substantially uniform bending stress distribution and a length sufficiently long to prevent the tip member from folding over as the elongate member adopts the preformed curved orientation in response to withdrawal of the stiffening element from the lumen.

In a further aspect of the present invention, a hearing prosthesis is disclosed. The hearing prosthesis comprises an elongate member, configured to be implanted into a duct of a recipient's cochlea, having a preformed curved orientation, proximal and distal ends, electrodes disposed thereon, and a longitudinally-extending lumen for receiving a stiffening element; and a tip member, extending distally from the distal end of the elongate member, having a substantially uniform bending stress distribution and a length sufficiently long to prevent the tip member from catching on the duct wall as the elongate member adopts the preformed curved orientation in response to withdrawal of the stiffening element from the lumen.

BRIEF DESCRIPTION OF THE DRAWINGS

Embodiments of the invention will be described in conjunction with the accompanying drawings, in which.

DETAILED DESCRIPTION

In one embodiment, the present invention provides an implantable tissue stimulating device, such as an electrode array, comprising: an elongate electrode carrier member (elongate member) having a body having a first end, and a resiliently flexible tip member extending distally from a distal end of the body. As used herein, a "distal" portion of an element is the leading portion of the element when it is inserted into the cochlea. The elongate member has at least one electrode mounted thereon to apply preselected tissue stimulation, such as stimulation of a nerve in a cochlea. The tip member includes a tapered portion tapering distally and a blunt end at a distal end of the tapered portion. In one embodiment of the present invention, the tip member includes a barrel portion at a proximal end of the tip member and the tapered portion extends distally from a distal end of the barrel portion. In a preferred embodiment, the tip member has a length of about 1.2 mm. As used herein, a "proximal" end of an element is the end opposite the distal end of the element. Additionally, as used herein, an element "tapering distally" refers to an element that is tapered such that the diameter of the element is smaller at the distal end of the element than at the proximal end.

In one embodiment of the present invention, the tip member may be formed of the same material as the body of the elongate member. In another embodiment, the tip member may be formed of a different material to that of the body of the elongate member.

The tip member may be formed separately to the body of the elongate member and mounted thereto. For example, the tip member may be adhered using an adhesive to the first end of the body of the elongate member. Alternatively, the tip member may be mounted on the tip member by other means such as by snapping the tip member over a mating distal end portion of the elongate member, screwing the tip member onto the end a threaded distal end of the elongate member, hot welding together the tip member and the elongate member, etc. In another embodiment, the tip member may be integrally formed with the body of the elongate member. The tip member may be formed from a silicone material. In another embodiment, the tip member may be formed of an elastomeric material, such as polyurethane. In general, the tip member is made of any material that allows the tip member to be resiliently flexible.

Figure 5:
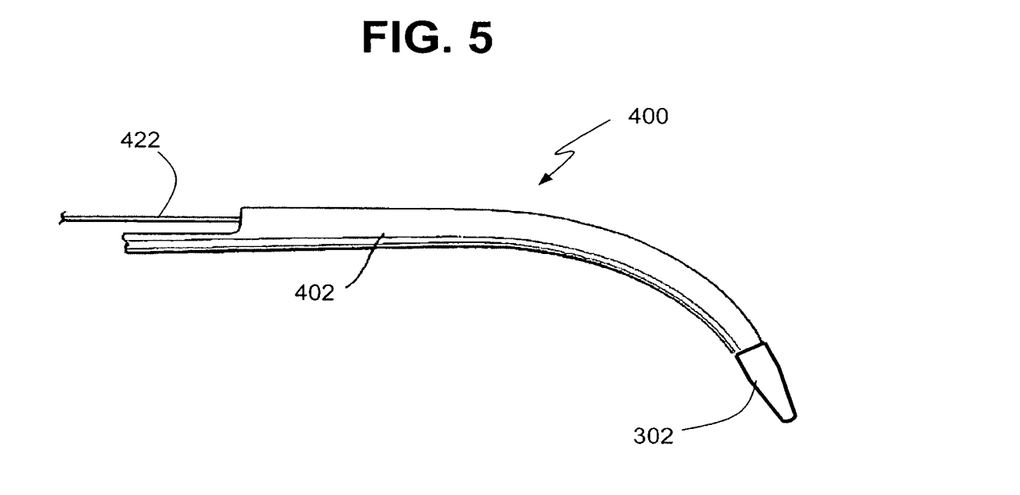
FIG. 5 is a simplified side elevational view of the electrode array of FIGS. 4A and 4B of the present invention depicted in an intermediate orientation.
Figure 7:
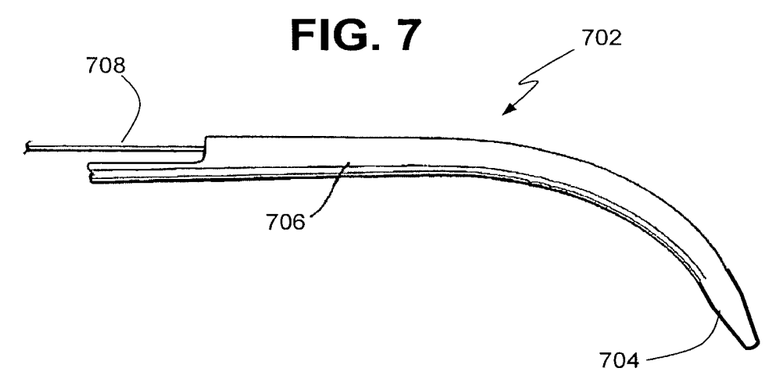
FIG. 7 is a simplified side elevation view of an electrode array in accordance with another embodiment of the present invention depicted in an intermediate orientation.

In some embodiments the barrel portion of the tip member may be part of a separate tip member that is joined to an elongate member, such as the embodiment of the present invention illustrated in FIGS. 5. In other embodiments, the tip member may be formed as part of an elongate member, such as the embodiment illustrated in FIG. 7. The elongate member may also have a taper, but the tapered portion of the tip member will taper at a faster rate than the overall taper of the elongate member. Examples of tapered elongate members are illustrated in FIGS. 5 and 7.

In one embodiment of the present invention, the barrel portion of a tip member may be substantially cylindrical in form, i.e., have a generally cylindrical shape, for a portion of its length. In another embodiment, the barrel portion may be substantially cylindrical in form. As used herein, an element may be "substantially cylindrical" and still include various raised or etched surface patterns and/or textures and may vary in width throughout the length of the part as long as the object has roughly the same diameter at the proximal and distal ends of the part. In other embodiments the barrel portion may be various shapes and include various types of contouring. The barrel portion also may have various types of cross-sections besides the circular cross-section of a cylindrical barrel. For example, the barrel portion may be elliptical in cross-section, rectangular with rounded corners in cross-section, triangular with rounded corners in cross-section, etc.

The barrel portion in some embodiments may be slightly tapered, but in such embodiments the tapered portion tapers at a faster rate than the barrel portion.

In one embodiment of the present invention, the barrel portion is about or exactly 0.4 mm in length from the proximal end of the barrel portion to the distal end of the barrel portion where the tapered portion begins. In one preferred embodiment where the barrel portion is cylindrical, the diameter of the barrel portion may be exactly or about 0.45 mm.

Figure 4A:
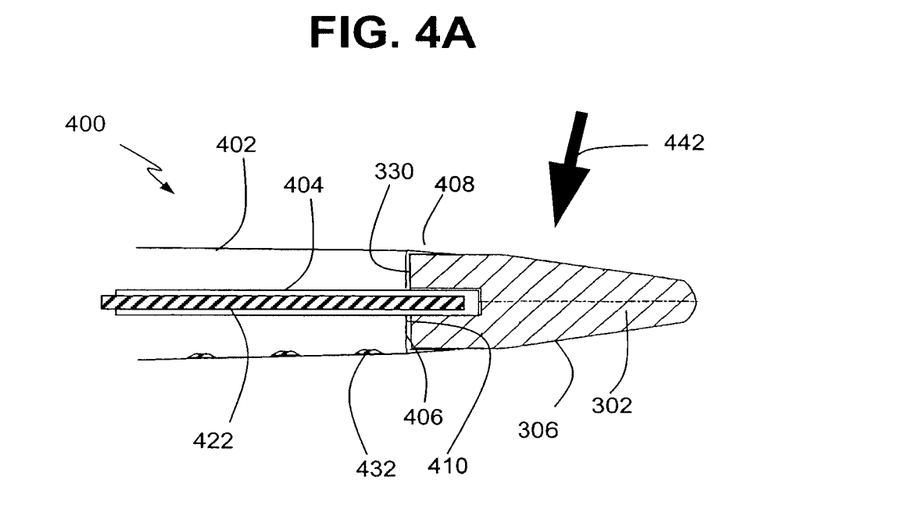
FIG. 4A is a cross-sectional view of an electrode array in accordance with one embodiment of the present invention in which tip member of FIGS. 3A and 3B are mounted on an elongate member with only a portion of the elongate member being shown for simplicity.
Figure 4B:
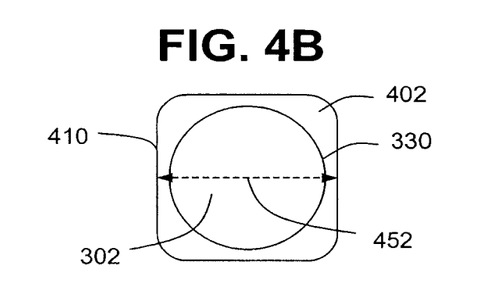
FIG. 4B is an end-on view of the electrode array of FIG. 4A.

In one embodiment for use with a tip member having a barrel portion with a 0.45 mm diameter the elongate member on which the tip member is mounted is slightly tapered and has a maximum diameter at its proximal end of about 0.80 mm and a minimum width or diameter at its distal end of about 0.5 mm. When the diameter of the distal end of the elongate member is larger than the diameter of the barrel portion or a different cross-sectional shape, such as illustrated in the embodiment of FIGS. 4A and 4B, various means may be used to ensure a smooth transition between the distal end of the elongate member and the barrel portion. For example, when a silicone adhesive is used to adhere the tip member to the elongate member, some of the silicone adhesive may be used on the surface of the barrel portion to form a tapered region filling the gap between the edges of the elongate member and the edges of the barrel portion as shown in FIG. 4A.

The barrel portion preferably includes a lumen therein that extends for some or all of the length of the barrel portion. An example of such a lumen is shown in the embodiment of the present invention illustrated in FIG. 3B. In one preferred embodiment, the lumen may be about 0.3 mm and have a diameter of about 0.125 mm. The lumen may be adapted to receive the distal end of a stiffening element, such as a stylet of the type typically used with cochlear implants. An example of a distal end of a stiffening element being received by a lumen is shown in the embodiment of the invention illustrated in FIG. 4A. The barrel portion preferably has a lumen therein that extends for some or all of its length. In one embodiment of the present invention, the lumen may be about 0.3 mm.

In one embodiment of the present invention, the tapered portion may be substantially frusto-conical in shape. In another embodiment, the tapered portion is frusto-conical in shape. In other embodiments, the tapered portion may be various tapered shapes that are continuously tapered or non-continuously tapered. A part of a device may be substantially frusto-conical and still include various raised or etched surface patterns and/or textures and may taper non-continuously as the object has a proximal or distal end that is narrower than the opposite end of the part.

For the purposes of the present invention, a part that tapers at a set rate throughout the length of the part has a "continuous taper". For example, a tapered portion of a tip member that is frusto-conical has a continuous taper in which the diameter of the tapered portion decreases at a fixed rate from the proximal end of the tapered portion to the distal end of the tapered portion. An example of a tapered portion of a tip member of the present invention having a continuous taper is illustrated in FIG. 5. Also, for the purposes of the present invention, a part that does not taper at a set rate throughout the length of the part the term has a "non-continuous taper". For example, a part that is substantially frusto-conical may have regions where the width of the part remains constant without tapering, but which, viewed as a whole, tapers from one end to the other end of the part in an axial direction.

In one preferred embodiment, the tapered portion of the tip member may be frusto-conical and has a length of about 0.76 mm and the diameter of tapered portion decreases from about 0.45 mm to exactly or about 0.2 mm. In one embodiment, the angle between notional diametrically opposed sides of a tapered portion that is frusto-conical is about or exactly about 18.9°. For the purposes of the present invention, the term "notional diametrically opposed sides" refers to the two opposing angled edges formed by cutting a tapered portion of a tip member of the present invention in half along the tapered portion's axis. The angle between two notional diametrically opposed sides is the angle formed by extending two lines from the opposed sides, one line from each side, in a distal direction until the lines meet. In another embodiment the frusto-conical tapered portion may have a length of about 0.76 mm. Over this length, the diameter of the frusto-conical portion decreases from 0.45 mm to 0.2 mm.

Although one type of tapered portion of the present invention is described above, the tapered portion of the present invention may have a shape other than frusto-conical and taper portions that are frusto-conical or substantially frusto-conical may have an angle between notional diametrically opposed sides that is greater or less than 18.9°.

In one embodiment of the present invention, the blunt end of the tip member is round in shape. In another embodiment, the blunt end of the tip member is spherical for a portion of its length. In other embodiments, the blunt end may have various blunt shapes such as ellipsoidal, paraboloidal, etc. The blunt end of a tip member of the present invention may be convex.

In one preferred embodiment, the blunt end is part-spherical in shape and has length of about 0.04 mm and a maximum diameter of about 0.2 mm where the blunt end meets the distal end of the tapered portion.

In one embodiment, the tip member is designed so that when the tip member is subject to a bending force, the moment of that force may be evenly distributed along the tip member and the bending stresses on the tip member are constant throughout its length. This even distribution provides a tip member that is resiliently flexible, i.e. that is not subject to foldover when the tip member is subject to a bending force, such as may occur during insertion of the tip member into a recipient of the device. For example, a resiliently flexible tip member will not undergo fold-over or bend backwards during insertion into a cochlea when exposed to usual insertion forces necessary to insert a tip member of an electrode array into a cochlea.

A tip member for which bending stresses on the tip member are constant throughout its length has a uniform bending stress distribution. A tip member that has a uniform bending stress distribution may be envisioned as, for example, a constant-strength cantilever beam where bending stresses throughout the beam are equal to those at the fixed end, that is, the junction of the tip member with the elongate member on which the tip member is mounted. In addition, a tip member may have a substantially uniform bending stress distribution in an axial direction, which is a direction along a line extending through an element between the distal and proximal ends of the device in either direction. Also, as used herein, an "axis" of an element is line through the middle of the element. The "long axis" of an element is the longest axis that may be drawn through the element, which may be the axis extending between the proximal and distal ends of an element.

In one embodiment the tissue-stimulating device may be a prosthetic hearing implant, such as the cochlear implants made by Cochlear Limited, with the elongate member comprising a carrier member for a plurality of electrodes. The tip member in this embodiment may be constructed to assist in the guiding of the elongate member into the cochlea, particularly into the scala tympani of the cochlea.

In another embodiment the elongate member may have a first configuration selected to allow the elongate member to be inserted into a recipient's cochlea and at least a second configuration wherein the elongate member is adapted to apply the preselected tissue stimulation. In one embodiment of the present invention, the elongated member in the first configuration is straight or substantially straight. However, in other embodiments, the elongated member in the first configuration may be curved.

In one embodiment of the present invention, the second configuration of the elongate member is curved. In another embodiment, the elongate member adopts a spiral configuration when in the second configuration. The body of the elongate member may be preformed from a plastic or rubber material with memory that is preformed to the second configuration.

The elongate member may be formed from a resiliently flexible material. In a further embodiment, the tip member is resiliently flexible. In one embodiment of the present invention, the tip member may be formed of a material having substantially the same or the same flexibility as the material used to form the body of the elongate member that encapsulates the electrode element(s) and wires.

In one embodiment of the present invention, the tip member may be formed of the same material as the body of the elongate member. In another embodiment, the tip member may be formed of a different material to that of the body of the elongate member. For example, the tip member may be formed of a material having a relatively lesser stiffness than a portion of the body of the elongate member. In another embodiment, the tip member may be formed of a material that undergoes a change in stiffness, preferably a decrease in stiffness, on insertion into the body, such as the cochlea.

The tip member may be made as a separate unit and then mounted on to a distal end of the elongate member. For example, the tip member may be adhered to the distal end of the body of the elongate member or be molded thereto in a secondary molding step. In one embodiment of the present invention, the tip member may be formed of an elastomeric material, such as polyurethane. The tip member may also be formed from a silicone material. In general the tip member may be made from any material such as plastic or rubber that allows the tip member to be resiliently flexible.

In one embodiment of the present invention, the body of the elongate member may be formed from a suitable biocompatible material. In one embodiment of the present invention, the material may be a silicone. In another embodiment, the body may be formed from a suitable elastomeric material, such as polyurethane or other biocompatible rubbers or plastics.

In another embodiment, the elongate member may have a receiving portion into which a stiffening element may be inserted. The device may further include a removable stiffening element positionable within the receiving portion of the elongate member and having a configuration selected for biasing the elongate member into the first configuration, described above. The stiffening element is preferably relatively stiffer than the elongate member.

In one embodiment, the receiving portion may comprise a lumen extending at least into, and more preferably through, the body of the elongate member. The lumen for the stylet may be cylindrical and also may have an opening formed therein proximal to the tip member. In the case of a metal stylet, the stylet may extend out of the opening allowing the stylet to be manipulated and removed from the lumen during or following insertion of the device.

In one embodiment the stiffening element is formed of a bioresorbable material which dissolves on exposure to a fluid. The stiffening element may dissolve on exposure to a saline solution or a body fluid of the implantee, such as cochlear fluid. In another embodiment, the bioresorbable material of the stiffening element is selected from the group consisting of polyacrylic acid (PAA), polyvinyl alcohol (PVA), polylactic acid (PLA) and polyglycolic acid (PGA).

In one embodiment of the present invention, the stiffening element may comprise a stiffening element formed from a non-bioresorbable material. In this embodiment, the stiffening element may comprise a metallic stylet extending through the receiving portion of the body of the elongate member. In one embodiment of the present invention, the wire may be formed from a biocompatible metal or metallic alloy. In one embodiment of the present invention, the stylet may be formed from platinum. Other suitable stiffening elements and stylets for use in the present invention are also described in U.S. Pat. No. 6,421,569, U.S. patent application Ser. No. 10/070,102 filed Jul. 8, 2002, and U.S. patent application Ser. No. 10/203,079 filed Oct. 17, 2001, the entire disclosures and contents of which are hereby incorporated by reference herein.

In one embodiment of the present invention, the stiffening element may be formed from a shape memory or heat sensitive material. For example, the stiffening element may be formed from a bimetallic element (such as nickel/titanium) and shaped to take a straight or substantially straight configuration at room temperature but bends into another shape once it is exposed to body temperature.

The construction of the electrode array of the present invention may be adapted to minimize the likelihood of trauma to the cochlea caused by insertion of the electrode array. The construction of the tip member is envisaged by the present inventors to assist in guiding the electrode down the lumen of the scala tympani of the cochlea. It is also envisaged that the construction of the tip member will minimize the potential for the tip member of the electrode to perforate the basilar membrane of the cochlea or damage other sensitive structures in the cochlea.

The tip member of the present invention is useful for those elongate members inserted in the cochlea using an Advance Off-Stylet™ (AOS™) mode of implantation. (ADVANCE OFF-STYLET and AOS are trademarks of Cochlear Limited, Lane Cove, NSW, Australia.) In this mode, the elongate member while mounted on a stylet is inserted through a cochleostomy until the tip member is positioned just short of the basal turn of the cochlea. Once the tip member has reached this position, the elongate member may be advanced or moved off the stylet and further into the scala tympani. As the elongate member is advanced off the stylet, the elongate member is also free to begin to adopt its preferential spiral curvature. The construction of the tip member of the present invention prevents foldover of the tip member as the tip member is moved off the stylet. The length of the tip member, however, is also sufficiently short to ensure that the tip member does not damage the walls of the scala tympani once the elongate member has reached its desired final insertion position in the cochlea.

Figure 1:
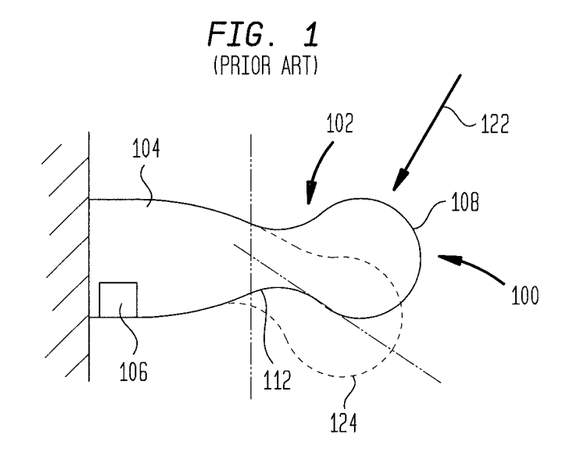
FIG. 1 is a force diagram of a prior art tip member used in electrode arrays.
Figure 2:
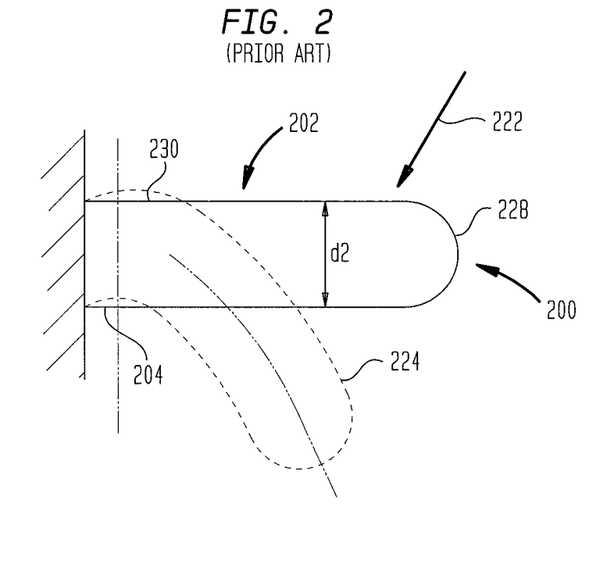
FIG. 2 is a force diagram of another prior art tip member used in electrode arrays.

FIGS. 1 and 2 represent force diagrams of typical tip members of known prior art electrode array carriers. It is possible from a review of these two diagrams to identify the problems with such prior art tip members.

FIG. 1 illustrates a prosthetic hearing implant device 100 including a tip member 102 that is essentially an extension of an electrode array carrier member 104. For simplicity, only a portion of electrode array carrier member 104 is illustrated in FIG. 1. Electrode 106 is the most distal electrode of electrode array carrier member 104. Tip member 102 has a bulbous distal end 108 a relatively narrow diameter neck section 112 which is designed to provide increased flexibility to tip member 102. As is shown, during insertion, a force (represented by arrow 122) is applied to tip member 102 when electrode array carrier member 100 comes into contact with the wall of the cochlea (not shown) during insertion. Due to the force represented by arrow 122, tip member 102 will flex about neck section 112 causing distal end 108 to undergo excessive deflection, indicated by ghost lines 124, greatly increasing the possibility of tip member 102 folding over upon itself during insertion.

FIG. 2 illustrates a prosthetic hearing implant device 200 including a tip member 202 having a constant cross-sectional diameter d2 along the length of tip member 202. Similar to tip member 102 shown in FIG. 1, tip member 202 is essentially an extension a carrier member 204 for the electrode array (not shown) beyond the position of the most distal electrode (not shown). As is shown, when a force represented by arrow 222 is applied to a distal end 228 of tip member 202, tip member 202 will flex about a location 230 where tip member 202 joins carrier member 204.

The design of the implant device illustrated in FIG. 2 increases flexibility due to the long arm of the impact force and as such there is an increased risk of such a tip member design causing array foldover and potential damage to the sensitive structures of the cochlea.

Figure 3A:
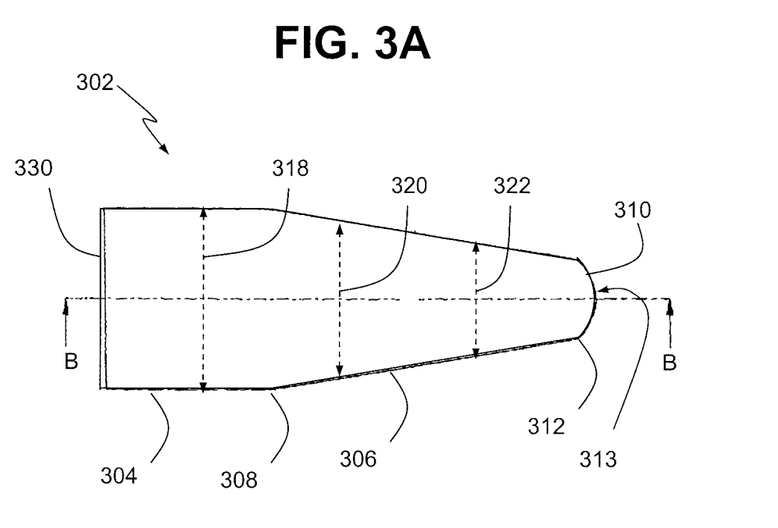
FIG. 3A is a side view of a tip member in accordance with an embodiment of the present invention.
Figure 3B:
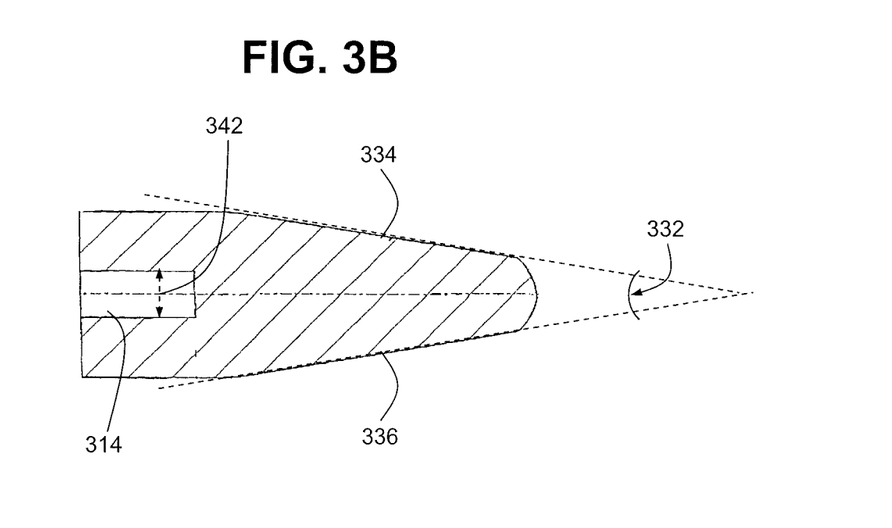
FIG. 3B is cross-sectional view of the tip member of FIG. 3A, taken along line B-B.

FIGS. 3A and 3B represent one embodiment of a tip member 302 of the present invention. Tip member 302 includes a cylindrical barrel portion 304, a frusto-conical tapered portion 306 at a distal end 308 of barrel portion 304 and a part-spherical blunt end 310 at distal end 312 of tapered portion 306. Blunt end 310 terminates at tip member distal end 313. Within cylindrical barrel portion 304 is a lumen 314 for receiving a stiffening element (not shown). Cylindrical barrel portion 304 has diameter 318 that is constant. In contrast, tapered portion 306 has a diameter that continuously decreases along the length of tapered portion 306, as illustrated by exemplary diameters 320 and 322. Tip member 302 is attached to a carrier member (not shown in FIG. 3) at a proximal end 330 of tip member 302. An angle 332 between notional diametrically opposed sides 334 and 336 of tapered portion 306 is 18.9°. Lumen 314 has a constant diameter 342.

In the embodiment depicted in FIGS. 3A and 3B, the tip member is constructed separately from the carrier member carrying the electrode array. This allows the tip member to more easily be constructed in a manner that ensures the parameters of the tip member are appropriately controlled to ensure that the tip member fulfils its designed purpose.

The tip member depicted in FIGS. 3A and 3B, may be constructed of any material that allows the tip member to be resiliently flexible.

The dimensions and shape of tip member shown in FIGS. 3A and 3B allows for smooth insertion of an electrode array to which the tip member is attached while preventing tip member foldover.

In one embodiment of the present invention, the barrel portion of the tip member shown in FIGS. 3A and 3B may be exactly or about 0.4 mm in length and the diameter of the barrel portion may be exactly or about 0.45 mm for all or at least some of its length.

In one embodiment, the lumen in the tip member of FIGS. 3A and 3B has a diameter of about 0.125 mm and a length of about 0.3 mm.

In one embodiment of the present invention, the tapered portion of the tip member of FIGS. 3A and 3B has a length of about 0.76 mm and over this length the diameter of the tapered portion decreases from about 0.45 mm to 0.2 mm.

In one embodiment of the present invention, the length of the part-spherical blunt end has a length of about 0.04 mm and over this length the diameter of blunt end decreases from about 0.2 mm to 0.0 mm at the very distal end of the blunt end.

FIGS. 4A and 4B illustrate an electrode array 400 in accordance with one embodiment of the present invention. Electrode array 400 includes tip member 302 mounted on an elongate member 402, only a portion of which is shown in FIG. 4A. Elongate member 402 includes a lumen 404 extending therethrough. Tip member 302 is held on elongate member 402 by means of a liquid silicone rubber adhesive 406. Filler portions 408 of adhesive 406 smooth the transition from elongate member 402 to tip member 302, because in this embodiment a distal end 410 of elongate member 402 has a larger diameter than tip member proximal end 330. For illustration purposes, the amount of adhesive 406 between elongate member distal end 410 and tip member proximal end 330 is exaggerated in the depiction in FIG. 4A. A stylet 422 inserted into elongate member extends through lumen 404 and into lumen 314 of tip member 302. Elongate member 402 is slightly tapered, but the taper of elongate member 402 is not as great as the taper of tapered portion 306 of tip member 302. Elongate member 402 includes electrodes 432 on one side of elongate member 402. During insertion into a cochlea (not shown), tip member 302 may be subject to an impact/deflection force represented by arrow 442. As illustrated in FIG. 4B, elongate member 402 has a rounded corner square shaped cross-section having a minimum width 452.

As illustrated in FIG. 4A, the tip member provides a smooth transition of flexibility from the relatively stiff portion of the carrier member containing the electrode elements and wires (not shown) to the more flexible blunt end of the tip member.

Although the elongate member shown in FIG. 4B has a rounded corner square shaped cross-section, the elongate member of the present invention may have various cross-sectional shapes such as circular, elliptical, rectangular, etc. and the cross-sectional shape of the elongate member may vary over the length of the elongate member.

FIG. 5 illustrates electrode array 400 in a curved orientation. Upon insertion of electrode array 400 into the scala tympani of the cochlea (not shown), the exposure of electrode array 400 to body temperature (about 37° C.) results in stylet 422 adopting a curved orientation. As stylet 422 adopts a curved orientation, elongate member 402 is free to also adopt the curved orientation as is depicted in FIG. 5.

Figure 6:
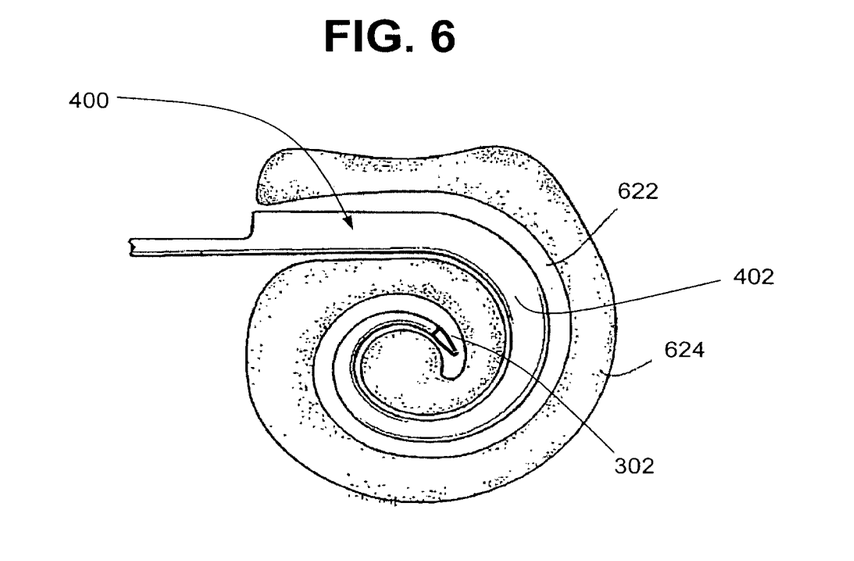
FIG. 6 is a simplified part sectional, part side elevational view of the electrode array of FIGS. 4A and 4B depicted in its pre-formed orientation following insertion in the cochlea.

As the elongate member 402 curls, the surgeon may continue to further insert electrode array 400 into scala tympani 622 of a cochlea 624 as illustrated in FIG. 6. During the further insertion process, the surgeon may commence withdrawal of stylet 422 from lumen 404 of elongate member 402. Alternatively, the surgeon may withdraw stylet 422 following complete insertion of electrode array 400 into its final position, this decision being dependent of the surgeon's preferences. Upon withdrawal of stylet 422, elongate member 402 is free to adopt its pre-formed spiral orientation, as depicted in FIG. 6, with electrodes 432 (not visible in FIG. 6) facing the modiola (not visible in FIG. 6) within cochlea 624 so that electrodes 432 are positioned as close as possible to the spiral ganglia thereof.

FIG. 7 illustrates an electrode array 702 of the present invention including a tip member 704 that is integral with an elongate member 706. A stylet 708 is inserted through a lumen in elongate member 706 and into a lumen in tip member 704. Electrode array 702 is essentially similar to electrode array 400 in both structure and function, except that tip member 704 is integral with elongate member 706 whereas in electrode array 400 tip member 302 is mounted on elongate member 402. As illustrated in FIG. 7, electrode array 702 is in a curved orientation, similar to the curved orientation of electrode array 400 in FIG. 5.

While an elongate member of the present invention, such as the elongate members of FIG. 5 and FIG. 7, may be manufactured with a preformed curved orientation, the device is typically delivered to a surgeon with the stylet in place. The stylet, while at room temperature, holds the elongate member in a straight orientation. A useful stylet for the purposes of the present invention may be a Nitinol wire.

Figure 8:
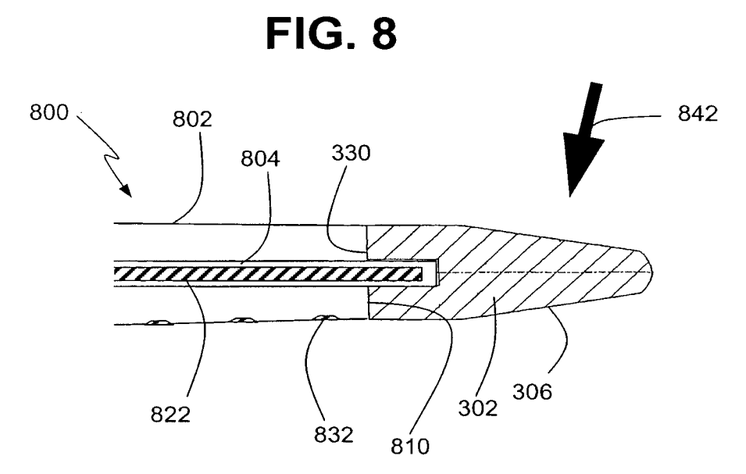
FIG. 8 is a cross-sectional view of an electrode array in accordance with one embodiment of the present invention in which tip member of FIGS. 3A and 3B are mounted on an elongate member with only a portion of the elongate member being shown for simplicity.

FIG. 8 illustrates an electrode array 800 in accordance with one embodiment of the present invention. Electrode array 800 includes tip member 302 mounted on an elongate member 802, only a portion of which is shown in FIG. 8. Elongate member 802 includes a lumen 804 extending therethrough. A distal end 810 of elongate member 802 has the same size diameter and is the same shape as tip member proximal end 330, so there is a smooth transition between elongate member distal end 810 and tip member proximal end 330. A stylet 822 inserted into elongate member extends through lumen 804 and into lumen 314 of tip member 302. Elongate member 802 is slightly tapered, but the taper of elongate member 802 is not as great as the taper of tapered portion 306 of tip member 302. Elongate member 802 includes electrodes 832 on one side of elongate member 802. During insertion into a cochlea (not shown), tip member 302 may be subject to an impact/deflection force represented by arrow 842.

In the electrode arrays of the present invention, such as the electrode arrays illustrated in FIGS. 5, 6 and 7, the stylet may have a preferred direction of curl on exposure to body temperature within the cochlea. In one embodiment, the electrode array may have an indicia means that provides an indication to a user, such as a surgeon, of the preferred direction of curl of the electrode array on implantation. This may be important as the electrode array is preferably oriented in the cochlea such that the direction of curl results in the electrode array being able to be moved into the scala tympani. The indicia means may comprise a loop formed in the wire at or adjacent a distal end thereof The loop as well as acting as an indicia means may act as a means of engaging with and withdrawing the stylet from the lumens in the elongate member and tip member during or following implantation. In one embodiment, the loop may be in the same plane as the preferred direction of curl of the stylet. The loop may extend away from the preferred direction of curl of the stylet.

In one embodiment of the present invention, it is possible to provide a sheath of bioresorbable and lubricious material, similar to the sheath described and shown in U.S. patent application Ser. No. 10/203,079, the entire disclosure and contents of which is hereby incorporated by reference herein. The bioresorbable material of stiffening sheath may be polyacrylic acid (PAA) that is adapted to dissolve on exposure to cochlear fluids. Other suitable bioresorbable materials may be envisaged and such materials need not necessarily dissolve on exposure to fluids. For example, the sheath may be made of a material that softens upon exposure to fluids but does not get absorbed.

As mentioned above, in one embodiment of the present invention, the tip member may be constructed separately from the elongate member of electrode array. In this regard, the tip member may be constructed out of a similar material to the body of the electrode array carrier such as silicone. To aid in fixing the tip member to the elongate member during production, the tip member lumen may be used to fit over a production stylet positioned within the lumen of the elongate member of the electrode array during its manufacture. Such a production stylet may be placed in a mold, along with the electrodes, and a suitable quantity of silicone is then poured into the mould around the stylet and electrodes to form the elongate member. In the present embodiment, the distal end of the production stylet would preferably extend a relatively short distance out of the distal end of the molded carrier member and act as a support for the tip member lumen of the tip member when the tip member is subsequently securely mounted on the distal end of the elongate member. A suitable production stylet and a method of manufacturing the elongate member of the electrode array of the present invention is described in more detail in U.S. Pat. No. 6,421,569, the entire disclosure and contents of which is hereby incorporated by reference herein.

Suitable elongate members for use with the tip member of the present invention and methods for inserting a device of the present invention into a cochlea are described in U.S. Pat. No. 6,421,569, U.S. patent application Ser. No. 10/070,102 filed Jul. 8, 2002, and U.S. patent application Ser. No. 10/203,279 filed Oct. 17, 2001, the entire disclosures and contents of which are hereby incorporated by reference herein.

The present invention provides a specifically designed tip of an electrode array that is shaped and dimensioned in a manner to optimize the flexibility of the array such that the tip will not undergo fold-over during insertion when exposed to usual insertion forces. This invention is a significant improvement over prior art attempts at providing such a flexible tip as embodiments of the present invention overcome the problem of the tip being too flexible at a critical section and becoming too flexible to enable smooth insertion of the array.

In one embodiment of the tip member of the present invention having a shape such as shown in FIGS. 3A and 3B, the design of the tip member may be based upon establishing the dimensions of three main parameters:

D1 is the diameter of the proximal end of the tip member that is connected to the elongate member;

D2 is the diameter of the distal end of the frusto-conical tapered portion; and

L is the length of the tip member.

The diameter D1 of the tip member in this embodiment at its proximal end that is connected to the end of the elongate member is preferably exactly or about 0.45 mm. This diameter allows the tip member to be easily fitted onto the end of a conventional electrode array, such as the Contour electrode array manufactured by Cochlear Limited of Lane Cove, New South Wales, Australia.

The diameter D2 of the distal end of the frusto-conical tapered portion of the tip member in this embodiment is preferably exactly or about 0.2 mm. This diameter has been determined based upon studies and experimental measurements of human cochlea and the sizes of the diameter of the outer wall of the cochlea as a dimension most likely to minimize the chance of the tip member penetrating the outer wall.

The length L of the tip member in this embodiment is preferably exactly or about 1.2 mm. Again, this dimension has been determined as being suitable for ensuring the tip fits within the appropriate region inside the cochlea for a range of initial electrode array insertion depths. It has been found that such a length of the tip member minimizes the likelihood of, and more preferably avoids, tip foldover for typical forces associated with electrode array insertion.

Having determined the important parameters of the tip of the present invention, namely D1, D2 and L, the shape of the tip member in this embodiment provides great flexibility whilst providing smooth mechanical interaction between the tip member and the cochlea thereby providing a smooth insertion procedure. The shape of the tip member in this embodiment takes into consideration the mechanical design requirements of the tip member. The shape and dimensions of the tip member of this embodiment is based on the idea of treating the tip member as a cantilever beam and determining the dimensions of a constant-strength cantilever beam where bending stresses throughout the beam are equal to those at the fixed end, that is, the junction of the tip member with the elongate member.

In this regard, the general stress formula for such a cantilever beam (assuming a rectangular cross-section) is:

$$\sigma = 6FL/(bh^2)$$

where $\sigma$ is the stress;

F is the deflection/impact force; and

L, b, h are the beam length, fixed end width, and height, respectively.

Assuming that the tip member is attached to a substantially tubular elongate member, the preferred cross-section of the tip member is circular, so that there is maximum alignment between the elongate member and the tip member when the tip member is attached to the elongate member during production. In this regard, for a circular beam the constant stress formula may be written as:

$$\sigma = k(\text{const.}) \times ((F.x)D^3)$$

where x is arm of force F (see FIG. 4A); and
D is the diameter for the circular beam.

Therefore, for a given impact/deflection force F (constant), in order to achieve uniform strength the following formula may be found:

$$X/D^3 = k'(\text{const.})$$

Therefore the formula for D as a function of x is:

$$D = k''(\text{const.}) \times \text{cube root}(x)$$

Given the abovementioned established parameters of the tip member, namely D1, D2 and L, the following equations may be determined:

$$0.2 = k''(\text{const}) \times \text{cube root}(x)$$

$$0.45 = k''(\text{const}) \times \text{cuberoot}(x=1.2)$$

As a result, in order to control the distribution of the force over the length of the tip member, the shape of the tip member of this embodiment may be approximated to the partially frusto-conical tapered shape as depicted in FIG. 3A.

All documents, patents, journal articles and other materials cited in the present application are hereby incorporated by reference herein.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An intra-cochlea electrode array comprising:
   an elongate carrier member;
   a plurality of electrodes spaced along the carrier member; and
   a flexible tip member disposed adjacent a distal end of the carrier member,
   wherein the tip member extends distally from the distal end of the carrier member, and wherein the tip member tapers distally, and
   wherein the flexible tip member comprises a blunt distal end, and wherein the tip member is substantially frusto-conical in shape.

2. The electrode array of claim 1, wherein the blunt distal end of the tip member has a first diameter and the distal end of the carrier member has a second diameter, and wherein the second diameter is at least 0.2 mm greater than the first diameter.

3. The electrode array of claim 1, wherein the tip member tapers continuously from the distal end of the carrier member to the blunt distal end.

4. The electrode array of claim 1, wherein the carrier member is pre-curved to position the electrodes adjacent the modiolus wall of the cochlea, and wherein:
   the carrier member defines a lumen,
   the lumen extends in an axial direction, and
   the lumen is configured to receive a stylet.

5. The electrode array of claim 4, wherein the lumen does not extend into the tip member.

6. The electrode array of claim 4, wherein:
   the lumen extends all the way to the distal end of the carrier member and into the tip member.

7. The electrode array of claim 1, wherein the tip member has substantially uniform bending stress distribution in an axial direction.

8. The electrode array of claim 1, wherein the tip member is a distinct portion of the array relative to the carrier member.

9. The electrode array of claim 1, wherein the tip member has a different functionality than the carrier member.

10. The electrode array of claim 1, wherein a majority of the outer diameters of the tip member are distinctly different from a diameter of the carrier member adjacent the tip member.

11. The electrode array of claim 1, wherein all the electrodes of the array are located on the carrier member.

12. An intra-cochlea electrode array comprising:
    an elongate carrier member having an axis and a first taper along the axis;
    a plurality of electrodes spaced along the carrier member; and
    a flexible tip member disposed proximate an end of the carrier member, wherein the tip member has a second taper greater than the first taper.

13. The intra-cochlear electrode array of claim 12, wherein the tip member comprises a distal end, and wherein the taper is substantially consistent to the distal end.

14. The intra-cochlear electrode array of claim 13, wherein the flexible tip member comprises a substantially cylindrical barrel portion, wherein the substantially cylindrical barrel portion is fixed to the elongate carrier member.

15. The intra-cochlear electrode array of claim 12, wherein the elongate carrier member comprises a first cross-sectional shape and wherein the flexible tip member comprises a second cross-sectional shape different than the first cross-sectional shape.

16. The intra-cochlear electrode array of claim 12, wherein the elongate carrier member comprises a first cross-sectional shape and wherein the flexible tip member comprises a second cross-sectional shape different than the first cross-sectional shape, and wherein the second cross-sectional shape is substantially round.

17. The intra-cochlear electrode array of claim 12, wherein the tip member has a lesser stiffness than a portion of the elongate carrier member.

18. The intra-cochlear electrode array of claim 12, wherein the elongate carrier member has a straight or substantially straight orientation, as opposed to a curved configuration.

19. The intra-cochlear electrode array of claim 12, wherein the elongate carrier member carries all of the electrodes of the intra-cochlear electrode array and wherein the intra-cochlear electrode array is part of a cochlear implant.

20. A cochlear implant, comprising:
    an intra-cochlea electrode array including a plurality of electrodes configured to stimulate tissue of a recipient of the cochlear implant, an electrode carrier section carrying the electrodes and a tip section, wherein the tip section is flexible and disposed adjacent a distal end of the carrier section, wherein
    the electrodes of the electrode array are spaced along the carrier section in a longitudinal direction of the array, and the tip section includes a proximal end disposed proximate the distal end of the carrier section, a part-spherical blunt end disposed opposite the proximal end and a continuous tapered portion between the proximal end and the part-spherical blunt end.

21. The cochlear implant of claim 20, wherein:
the tip section tapers distally.

22. The cochlear implant of claim 20, wherein the tip section does not exceed 1.2 mm in length.

* * * * *